(12) United States Patent
Yamaguchi et al.

(10) Patent No.: US 7,151,602 B2
(45) Date of Patent: Dec. 19, 2006

(54) PARTICLE SIZE DISTRIBUTION ANALYZER

(75) Inventors: Tetsushi Yamaguchi, Kyoto (JP); Makoto Umezawa, Kyoto (JP)

(73) Assignee: Horiba, Ltd., Kyoto (JP)

( * ) Notice: Subject to any disclaimer, the term of this patent is extended or adjusted under 35 U.S.C. 154(b) by 439 days.

(21) Appl. No.: 10/718,068

(22) Filed: Nov. 20, 2003

(65) Prior Publication Data

US 2004/0100630 A1 May 27, 2004

(30) Foreign Application Priority Data

Nov. 21, 2002 (JP) .......................... P2002-338627

(51) Int. Cl.
*G01N 15/02* (2006.01)
(52) U.S. Cl. ...................... 356/336; 356/335
(58) Field of Classification Search ................ 356/336, 356/342, 436, 440, 441, 442; 250/574, 573, 250/576, 222.2
See application file for complete search history.

(56) References Cited

U.S. PATENT DOCUMENTS 5,172,004 A * 12/1992 Furuya ........................ 250/564
5,416,580 A    5/1995 Trainer
5,696,580 A *  12/1997 Kubo et al. .................... 356/72
6,091,492 A *   7/2000 Strickland et al. .......... 356/336
6,404,493 B1 *  6/2002 Altendorf ..................... 356/337
6,465,802 B1 * 10/2002 Matsuda ....................... 250/574

FOREIGN PATENT DOCUMENTS

| JP | 62-058138   |   | 3/1987  |
|----|-------------|---|---------|
| JP | 02-212741   |   | 8/1990  |
| JP | 6-12942     |   | 2/1994  |
| JP | 06-221989   |   | 8/1994  |
| JP | 08-178825   |   | 7/1996  |
| JP | 09-033423   |   | 2/1997  |
| JP | 10-213534   |   | 8/1998  |
| JP | 2002-005813 |   | 1/2002  |
| JP | 2002-221479 | * | 8/2002  |
| JP | 2003-329570 |   | 11/2003 |
| WO | WO 01/61313 A3 | | 8/2001 |

* cited by examiner

*Primary Examiner*—Gregory J. Toatley, Jr.
*Assistant Examiner*—Roy M. Punnoose

(57) ABSTRACT

A dynamic particle size distribution analyzer includes a transparent cell for receiving the sample, a laser light irradiating section and a scattering light detecting section. The transparent cell incorporates a configuration to the walls of the transparent cell to reduce any noise causing scattering light incident on the light detecting section.

14 Claims, 3 Drawing Sheets

PARTICLE SIZE DISTRIBUTION ANALYZER

BACKGROUND OF THE INVENTION

1. Field of the Invention

The present invention relates to dynamic light scattering particle size distribution analyzers.

2. Description of the Related Art

The so-called "dynamic light scattering particle size distribution analyzer", as disclosed in Japanese Patent Laid-Open Publication No. 2002-221479, is known as a device for measuring the particle diameters of small particles. This type of device analyzes a particle size distribution based on the following measuring principle. That is, in a sample containing a certain concentration of particles to be measured, the particles move irregularly (Brownian motion) in a solvent with the tendency that relatively large particles move slowly while relatively small particles move quickly. When the sample is irradiated with laser light having a fixed frequency, the laser light is scattered with the particles. Since the particles are individually in Brownian motion as described above, the frequency of scattering light from each particle shifts slightly from the frequency of incident light depending on the motion velocity of each particle due to Doppler shift.

Therefore, measurement of such shifts in frequency makes it possible to determine the particle size distribution of the sample statistically. Specifically, the total sum of frequency shifts of scattering light from all the particles is observed as a "fluctuation" in the intensity of scattering light and, hence, the particle size distribution of the sample can be calculated from such a fluctuation by using an algorithm exclusive to this type of calculation.

However, such scattering light takes place not only at the particles to be measured but also at various other sites such as scratches of a cell containing the aforementioned sample, the interface between the cell and outside air or between the cell and the sample, and the like. Such scratches and interfaces are fluctuated due to 1/f fluctuation occurring in nature, minute fluctuations of the cell, presence of surface tension wave, or the like. Scattering light from such scratches and interfaces are also subject to frequency shifts due to such fluctuations and hence cause noise to occur, which affects the measurement.

With a sample having a relatively high concentration, scattering light from particles to be measured are predominant. Signals generated by noise light scattered from the aforementioned scratches and the like are of negligible levels because they are buried in optical fluctuation signals from the particles. However, in the case of a sample having a relatively low concentration of particles to be measured or a sample containing fine particles, signals generated by noise-causing scattering light is of levels that cannot be neglected and as a whole suffers from such a problem as to lower the measurement precision or the SN ratio, which might result in impossibility of effective measurement.

With a view to overcoming this problem, a dynamic light scattering particle size distribution analyzer has heretofore been developed of the immersed cell type in which a cell is immersed in a liquid having a refractive index approximately equal to that of the cell in order to reduce noise-causing scattering light occurring at the interface between the outside surface of the cell and outside air due to a difference in refractive index.

Such an analyzer, however, cannot effectively eliminate noise-causing scattering light caused by scratch or deflection of the cell wall and noise-causing scattering light occurring at the interface between the inside surface of the cell and the sample contained therein, though it is capable of eliminating noise-causing scattering light occurring at the interface between the outside surface of the cell and the outside air interface. Particularly recently, heavy use has been made of a disposable cell made of a resin such as a plastic. Such a cell is susceptible to scratch, deflection, or streak resulting from heterogeneity of a plastic and appearing like a string in the cell wall, which are responsible for the occurrence of noise-causing scattering light Further, the immersed cell type analyzer often uses an organic solvent to immerse the cell. Such an organic solvent is difficult to handle and often requires that the structure of the analyzer be made complicate. In addition, dust or contaminant, which is possibly mixed into the solvent, may cause noise-causing scattering light to occur.

Accordingly, it is an object of the present invention to provide a dynamic light scattering particle size distribution analyzer having a very simple structure capable of reducing noise-causing scattering light that is responsible for the occurrence of noise.

SUMMARY OF THE INVENTION

In order to accomplish the aforementioned object, the present invention provides a particle size distribution analyzer including a transparent cell for containing a sample containing particles to be analyzed, a laser light irradiation section for irradiating the sample with laser light from outside of the cell, a scattering light intensity detecting section for detecting the intensity of scattering light from the particles irradiated with laser light, a calculating section for calculating a particle size distribution of the particles based on a fluctuation of the intensity of scattering light measured which occurs due to Brownian motions of the particle, and a noise reducing section operative to reduce the amount of noise-causing scattering light becoming incident on the scattering light intensity detecting section, the noise reducing section comprising a region to be irradiated with laser light of at least one of outside surface and inside surface of the cell, the region being inclined a predetermined angle with respect to the optical axis of laser light.

The term "noise-causing scattering light", as used herein, is meant to include scattering light that is caused by scratch of the cell, the difference in refractive index between the cell and outside air, or the like. Also, the term "inclined", as used herein, is meant express a state where the wall surface forms an angle except 90 degrees with the optical axis of laser light.

Such a construction can employ a very simple arrangement such that an existing cell, for example, is mounted at a different angle than in a conventional analyzer, to realize a large reduction in the influence on measurement from noise-causing scattering light which is caused by minute unevenness (scratch) on the cell surface or streaks in the cell wall or which occurs at the interface between the outside surface of the cell and outside air or at the interface between the inside surface of the cell and the sample due to a difference in refractive index between them. Since the intensity distribution direction of such noise-causing scattering light greatly depends on the angle of irradiation of laser light on the outside surface or inside surface of the cell, inclining the outside surface or inside surface of the cell will make it possible to cause noise-causing scattering light to travel in directions different from the direction of the optical axis of scattering light to be measured.

Further, such an inclined cell wall surface is capable of reliably cutting the amount of light reflected toward the scattering light intensity detecting section by the cell wall surface, thereby largely reducing the noise component derived from reflected light.

Thus, the analyzer of the present invention can lower the noise level substantially and hence is capable of effectively analyzing even a sample having a very low particle concentration.

In a specific embodiment of the present invention which makes the effect of the invention more noticeable, the scattering light intensity detecting section is configured to measure the intensity of back scattering light which travels in reverse of a direction of irradiation of laser light on the sample. The expression "back scattering light which travels in reverse of a direction of irradiation of laser light on the sample", as used herein, is meant to include light rays having directional components reverse to the direction of irradiation of laser light.

The foregoing and other objects, features and attendant advantages of the present invention will become apparent from the reading of the following detailed description in conjunction with the accompanying drawings.

DETAILED DESCRIPTION OF THE PREFERRED EMBODIMENTS

The present invention will now be described in detail with reference to the drawings.

Figure 1:
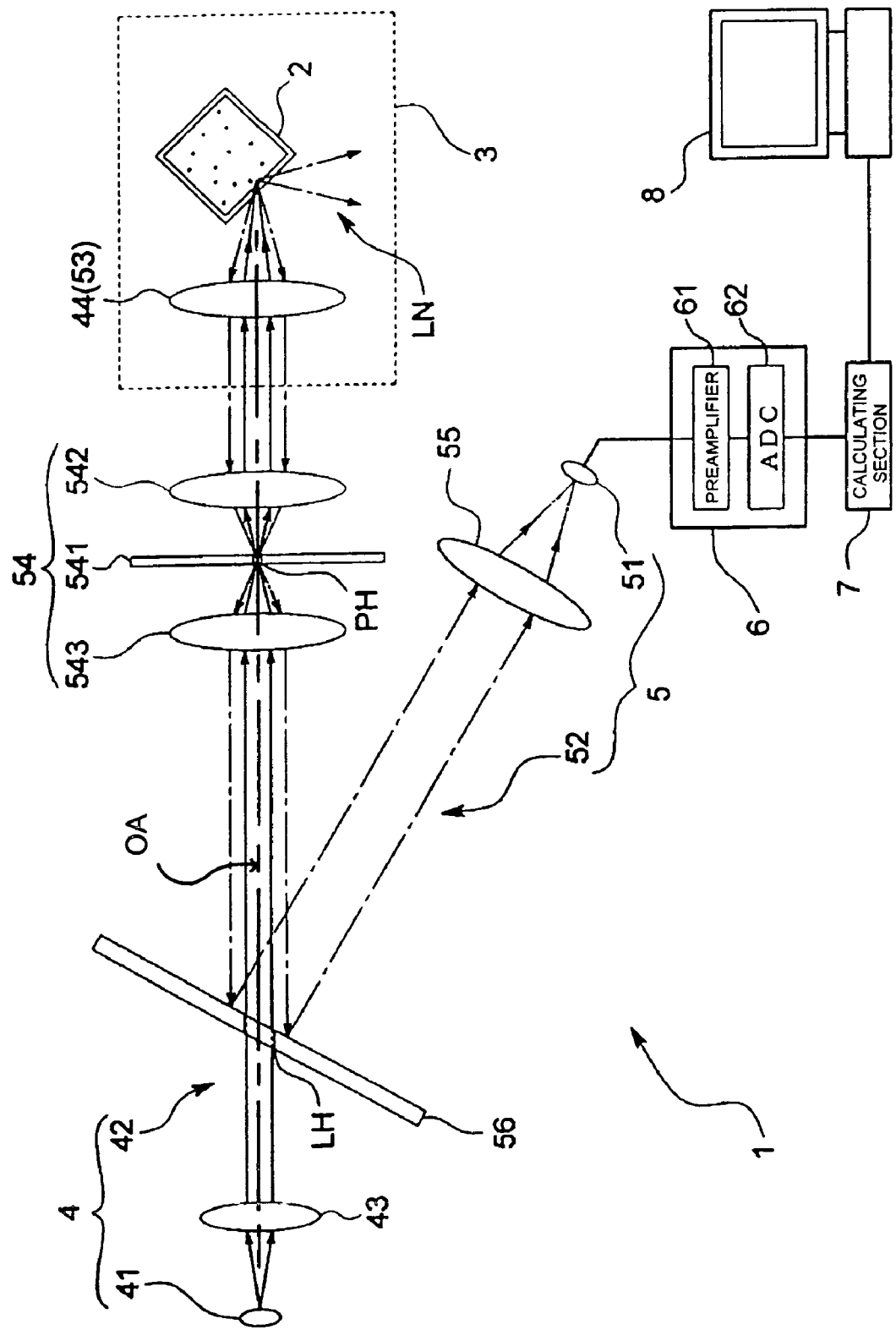
FIG. 1 is a schematic view illustrating the overall construction of a dynamic light scattering particle size distribution analyzer in accordance with one embodiment of the present invention.
Figure 2:
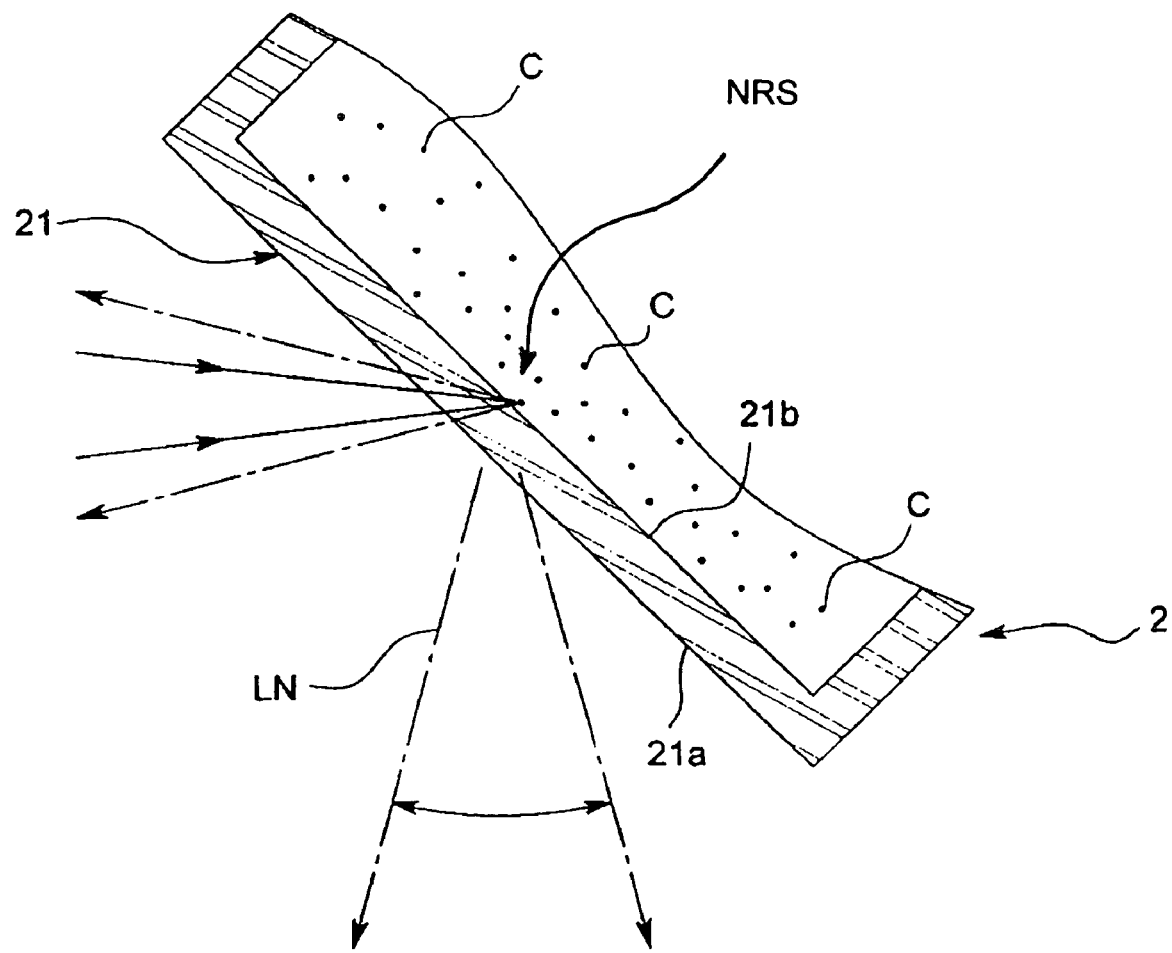
FIG. 2 is an enlarged fragmentary sectional view of a relevant portion of the analyzer shown in FIG. 1.

Referring to FIGS. 1 and 2, there is shown a particle size distribution analyzer 1 of the dynamic light scattering type according to one embodiment of the present invention. The analyzer 1 includes a transparent cell 2 for containing a sample containing particles C to be measured, a cell unit 3 holding the transparent cell 2 therein, a laser light irradiating section 4 for irradiating the sample with laser light along an optical axis, QA, having a certain frequency from outside of the cell 2, a scattering light intensity detecting section 5 for detecting the intensity of light scattering from the particles irradiated with laser light and outputting the intensity detected as an intensity signal, an intensity signal receiving section 6 for receiving the intensity signal, and a calculating section 7 for calculating the particle size distribution of the particles C based on a fluctuation of the intensity signal received by the intensity signal receiving section 6.

Description will be made of each part of the analyzer 1.

The cell 2 includes, for example, a hollow rectangular parallelepiped transparent glass member having a uniform thickness and is removably held by a non-illustrated cell holder provided in the cell unit. The sample contained in the cell 2 is a dispersion containing a relatively low concentration of particles C in a dispersing medium such as water. The particle concentration may be relatively high when the particles C are fine. Since Brownian motions of the particles C in the sample vary sensitively with change in temperature, which may affect the measurement, this embodiment is provided with a temperature control mechanism (not shown) for controlling the temperature within the cell unit 3 to stabilize the temperature of the sample under measurement, thereby realizing high-precision measurement.

The laser light irradiating section 4 includes a light source of laser light having a semiconductor laser 41 for example, and a light guide mechanism 42 defining an optical axis, OA, for guiding laser light irradiated from the semiconductor laser 41 to the sample. The light guide mechanism 42 includes a collimator lens 43 for turning diffused laser light irradiated from the semiconductor laser 41 into a beam of parallel laser light having a certain diameter, and a condenser lens 44 for condensing the beam of parallel laser light onto a predetermined irradiated region set at a location slightly inwardly of the inside surface of the cell 2.

The scattering light intensity detecting section 5 includes a photodetector 51 for receiving light of a predetermined wave range and outputting an intensity signal which is an electric signal corresponding to the intensity of light received, and a scattering light guide mechanism 52 defining an optical axis for guiding scattering light, which scattered from the particles C, to the photodetector 51.

The scattering light guide mechanism 52 functions to cause scattering light, which is scattered in a direction opposite to the traveling direction of incident laser light by particles C present in the aforementioned irradiated region, to travel in reverse to the traveling direction of incident laser light along the same optical axis up to some midpoint. The scattering light guide mechanism 52 includes a paralleling lens 53 for turning scattering light into a beam of parallel light having a larger diameter than the aforementioned beam of parallel laser light, a noise light cutoff portion 54 for cutting off noise light such as multiple scattering light from the beam of paralleled scattering light, and a second condenser lens 55 for condensing the scattering light outgoing from the noise light cutoff portion 54 onto the light-receiving surface of the photodetector 51. The paralleling lens 53 also serves as the aforementioned condenser lens 44, so that the optical axis of scattering light coincides with the optical axis of incident laser light up to some midpoint.

The noise light cutoff portion 54 includes a shielding plate 541 having a pinhole PH, and a pair of convex lenses 542 and 543 positioned on opposite sides of the shielding plate 541. The noise light cutoff portion 54 functions to condense the beam of paralleled scattering light into the pinhole PH with one lens 542 and then again parallel the beam of scattering light re-diffusing after having passed through the pinhole PH with the other lens 543.

This embodiment further includes a reflecting mirror 56 between the noise light cutoff portion 54 and the second condenser lens 55 for reflecting scattering light outgoing from the noise light cutoff portion 54 so that it can be received by the light-receiving surface of the photodetector 51 through the second condenser lens 55. Since the reflecting mirror 56 is disposed on the optical axis of the beam of parallel laser light, the reflecting mirror 56 centrally defines a laser light passing hole LH having a diameter generally equal to the diameter of the beam of parallel laser light so as to allow the beam to pass therethrough without varying the amount of parallel laser light.

The intensity signal receiving section 6 comprises a preamplifier 61 and an A/D converter 62 as basic components and functions to receive the intensity signal inputted as an analog signal and output a digital signal converted from the analog signal.

The calculating section 7 functions to calculate the particle size distribution of the particles C based on a fluctuation of the intensity signal outputted from the intensity signal receiving section 6 and then output the result of calculation in a predetermined form to a display or a printer through an information processing device 8 such as a personal computer. While this embodiment employs a homodyne detection method utilizing fluctuations resulting from interference between light scattered from the particles C, it is needless to say that the present invention may employ a heterodyne detection method. It should be noted that since the details of the calculating section 7 and the algorithm used in the calculating section 7 have been described in Japanese Patent Laid-Open Publication No. 2000-171383 and the like by the inventors of the present invention, description thereof is herein omitted.

In this embodiment, at least a region of the cell 2 which is to be irradiated with laser light and allows laser light to pass therethrough is inclined a certain angle with respect to the optical axis of the laser light. Specifically, the mounting angle of the whole cell 2 is set so that front wall 21 of the cell 2 on which laser light becomes incident forms an angle of 45 degrees for example with the optical axis of the incident laser light.

This arrangement makes it possible to largely reduce noise-causing scattering light, LN, which is caused by fine unevenness (scratch) on the surface of the cell 2 or streaks in the cell wall or which occurs at the interface between the outside surface $21a$ of the cell 2 and outside air or between the inside surface $21b$ of the cell 2 and the sample due to the difference in refractive index between them, as compared to an arrangement where the front wall 21 of the cell is positioned normal to the optical axis of laser light, that is, the front wall 21 forms an angle of 90 degrees with the optical axis of laser light. For example, such noise-causing scattering light can be reduced to $1/100$. This noise reducing section, NRS, can be seen by the alignment of the cell wall 21 shown in FIG. 2.

The intensity of such noise-causing scattering light greatly depends on the angle of irradiation of laser light on the outside surface $21a$ or inside surface $21b$ of the cell 2. In the aforementioned arrangement where the front wall 21 is positioned normal to the optical axis of laser light, laser light that has become incident on the front wall 21 scatters intensely in the direction just opposite to the direction of irradiation of laser light, thus causing a high level of noise. In contrast, the arrangement where the front wall 21 is inclined as shown in FIGS. 1 and 2 causes the traveling direction of noise-causing scattering light including the angle of diffusion of the noise-causing scattering light to differ from the direction of irradiation of laser light, i.e. the direction of the optical axis of scattering light to be detected.

Further, this embodiment is capable of reliably cutting off light reflected by the cell wall surfaces $21a$ and $21b$, hence, reducing the noise component derived from such reflecting light.

As described above, this embodiment is further provided with the noise light cutoff portion 54 and hence is capable of cutting off noise-causing scattering light that is scattered at locations other than the predetermined irradiated region located adjacent the inside surface $21b$ of the cell 2 into which laser light is to be condensed, as well as multiple scattered light. Accordingly, this embodiment can be expected to exhibit a noise reducing action based on synergy with the noise light cutoff portion 54.

As a result, this embodiment makes it possible to analyze the particle size distribution of even a sample having a very low particle concentration (for example $1/100$ of a conventionally analyzable concentration) effectively.

It is to be noted that the present invention may be modified variously.

Figure 3:
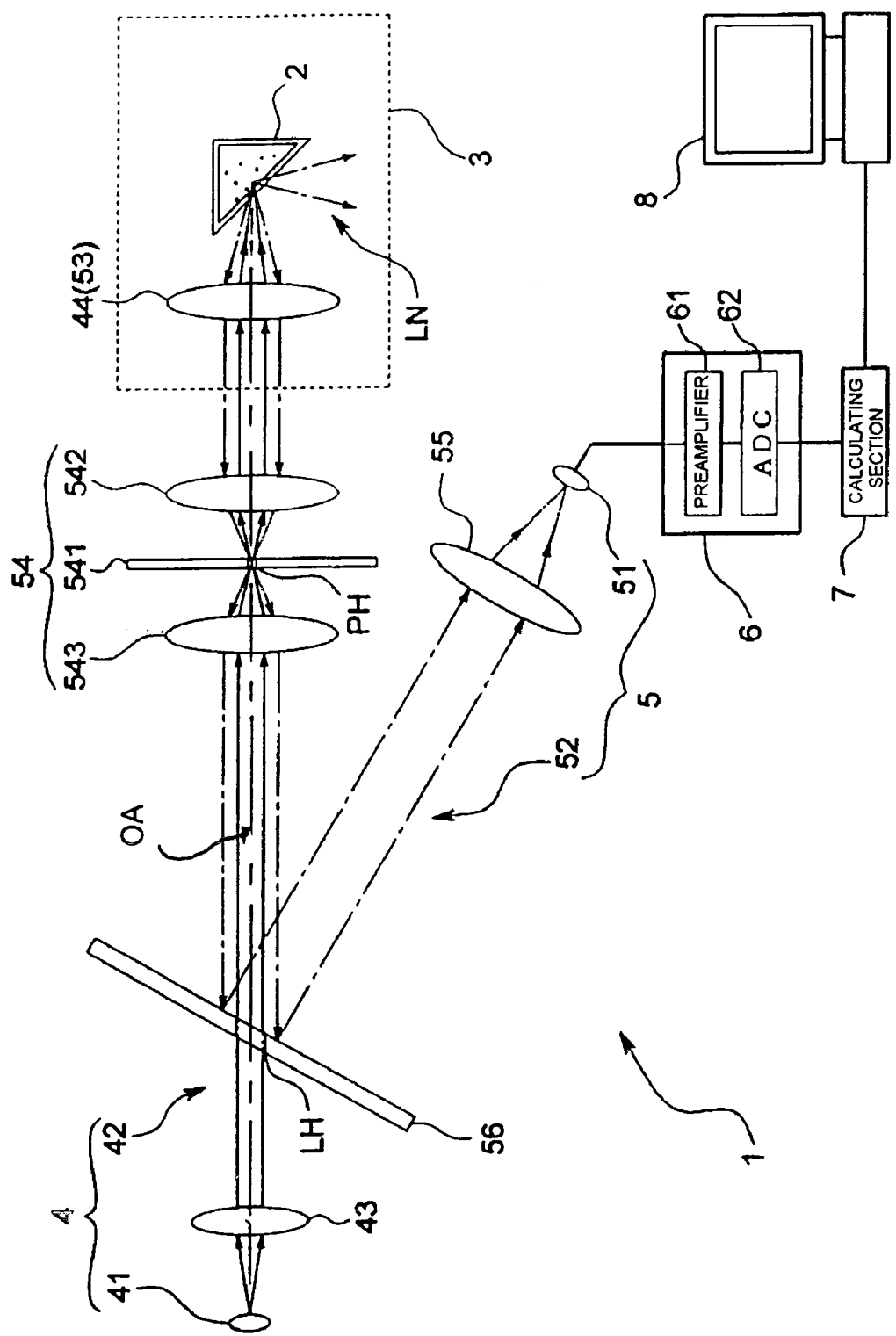
FIG. 3 is a schematic view illustrating the overall construction of a dynamic light scattering particle size distribution analyzer in accordance with another embodiment of the present invention.

For example, though the existing cell is mounted at an angle different from the conventional mounting angle in this embodiment, it is possible to make the angle of irradiation of laser light different from the conventional angle of irradiation of laser light. Further, the cell may be configured into a triangular prism as shown in FIG. 3. The essential feature of the present invention is that at least a region to be irradiated with laser light of the outside surface and/or inside surface of the cell and the optical axis of laser light are inclined a predetermined angle relative to each other.

Of course, the wall of the cell need not necessarily have a uniform thickness and only one of the inside surface and outside surface of the cell may be inclined relative to the optical axis of irradiation of laser light. Such an arrangement can also produces a desired noise reducing effect. Further, the noise light cutoff portion is not necessarily needed and hence may be eliminated in view of the principle of the invention.

According to the present invention having been described in detail, a very simple arrangement such that an existing cell, for example, is mounted at a different angle than in a conventional analyzer, makes it possible to largely reduce the influence on measurement by noise-causing scattering light which is caused by minute unevenness (scratch) on the cell surface or streaks in the cell wall or which occurs at the interface between the outside surface of the cell and outside air or between the inside surface of the cell and the sample due to the difference in refractive index between them. Since the intensity distribution direction of such noise-causing scattering light greatly depends on the angle of irradiation of laser light on the outside surface or inside surface of the cell, inclining the outside surface or inside surface of the cell will make it possible to cause noise light to travel in a direction different from the direction of the optical axis of scattering light to be measured.

Thus, the analyzer of the present invention can lower the noise level substantially and hence is capable of effectively analyzing the particle size distribution of even a sample having a very low particle concentration or containing fine particles.

While only certain presently preferred embodiments of the present invention have been described in detail, as will be apparent for those skilled in the art, certain changes and modifications may be made in embodiments without departing from the spirit and scope of the present invention as defined by the following claims.

What is claimed is:

1. A particle size distribution analyzer comprising:
   a transparent cell for containing a sample containing particles to be analyzed;
   a laser light irradiating section for irradiating the sample with a laser light from outside of the cell;
   a scattering light intensity detecting section for detecting the intensity of light scattered from the particles irradiated with the laser light;
   a calculating section for calculating a particle size distribution of the particles based on a fluctuation of the intensity of scattering light measured which occurs due to Brownian motions of the particles; and
   a noise reducing section operative to reduce the amount of noise-causing scattering light becoming incident on the scattering light intensity detecting section, the noise reducing section comprising a region to be irradiated with the laser light of at least one of an outside surface and an inside surface of the cell, the region being inclined a predetermined angle with respect to an optical axis of the laser light.

2. The particle size distribution analyzer in accordance with claim 1, wherein the scattering light intensity detecting section is configured to measure the intensity of back scattering light which travels in a reverse direction from a direction of irradiation of laser light on the sample.

3. The particle size distribution analyzer of claim 1 wherein the noise reducing section further includes a shielding plate with a pinhole positioned between the transparent cell and the scattering light intensity detecting section.

4. The particle size distribution analyzer of claim 1 wherein the transparent cell has four walls with an incident and egressing wall, for laser light transmission, the incident and egressing wall is positioned non-traverse to the optical axis of the laser light.

5. The particle size distribution analyzer of claim 1 wherein the transparent cell has three walls with an incident and egressing wall, for laser light transmission, the incident and egressing wall is positioned non-traverse to the optical axis of the laser light.

6. The particle size distribution analyzer of claim 1 wherein the outside surface and inside surface of the cell are parallel.

7. A particle size distribution analyzer comprising:
a transparent cell for containing a sample containing particles to be analyzed;
a laser light irradiating section for irradiating the sample with laser light from outside of the cell;
a scattering light intensity detecting section for detecting an intensity of light scattered from the particles irradiated with the laser light; and
a calculating section for calculating a particle size distribution of the particles based on a fluctuation of the intensity of scattering light measured, wherein the transparent cell has a planar wall that is positioned at an angle offset from a perpendicular crossing of an optical axis of the incident laser light to reduce any scattered light from defects in the surfaces of the planar wall to reduce noise—causing scattering light from the defects from reaching the scattering light intensity detecting section.

8. The particle size distribution analyzer in accordance with claim 7, wherein the scattering light intensity detecting section is configured to measure the intensity of back scattering light which travels in a reverse direction to a direction of irradiation of the laser light on the sample.

9. The particle size distribution analyzer of claim 7 wherein the noise reducing section further includes a shielding plate with a pinhole positioned between the transparent cell and the scattering light intensity detecting section.

10. The particle size distribution analyzer of claim 7 wherein the transparent cell has four walls with an incident and egressing wall for laser light transmission the incident and egressing wall is positioned non-traverse to the optical axis of the laser light.

11. The particle size distribution analyzer of claim 7 wherein the transparent cell has three walls with an incident and egressing wall for laser light transmission the incident and egressing wall is positioned non-traverse to the optical axis of the laser light.

12. The particle size distribution analyzer of claim 7 wherein the outside surface and inside surface of the cell wall are parallel.

13. A particle size distribution analyzer comprising:
a transparent cell for containing a sample containing particles to be analyzed;
a laser light irradiating section for irradiating the sample with a laser light along an optical axis from outside of the cell;
a scattering light intensity detecting section for detecting the intensity of light scattered from the particles irradiated with laser light; and
a calculating section for calculating a particle size distribution of the particles based on a fluctuation of the intensity of scattering light measured which occurs due to Brownian motions of the particles, a region to be irradiated with laser light of at least one of an outside surface and an inside surface of the cell being inclined a predetermined angle with respect to the optical axis of the laser light in order to reduce the amount of noise-causing scattering light caused by any scratch on the cell surface or streaks in a cell wall from becoming incident on the scattering light intensity detecting section.

14. A particle size distribution analyzer comprising:
a transparent cell for containing a sample containing particles to be analyzed;
a laser light irradiating section for irradiating the sample with a laser light along an optical axis from outside of the transparent cell;
a scattering light intensity detecting section for detecting the intensity of light scattered from the particles irradiated with the laser light; and
a calculating section for calculating a particle size distribution of the particles based on a fluctuation of the intensity of scattering light measured wherein the transparent cell has a planar wall that is positioned at an angle offset from a perpendicular crossing of the optical axis to reduce any scattered light from defects in the surfaces of the planar wall to thereby reduce noise-causing scattering light caused by a scratch on a cell surface or streaks in a cell wall from reaching the scattering light intensity detecting section.

* * * * *